US005474927A

United States Patent [19]
Anderson et al.

[11] Patent Number: 5,474,927
[45] Date of Patent: Dec. 12, 1995

[54] COMPLEMENT COMPONENTS AND BINDING LIGANDS IN FERTILITY

[75] Inventors: Deborah J. Anderson, Brookline, Mass.; Peter M. Johnson, Merseyside, England; Richard M. Jack, Brighton, Mass.

[73] Assignee: Brigham and Women's Hospital, Boston, Mass.

[21] Appl. No.: 137,820

[22] Filed: Oct. 19, 1993

Related U.S. Application Data

[63] Continuation of Ser. No. 487,039, Mar. 2, 1990, abandoned.

[51] Int. Cl.$^6$ .................................................. G01N 33/554
[52] U.S. Cl. .................. 435/7.21; 435/806; 436/510; 436/519; 436/65; 436/821; 436/906
[58] Field of Search ........................ 435/7.2, 7.21, 435/806; 436/518, 519, 65, 84, 906, 510

[56] References Cited

U.S. PATENT DOCUMENTS

| | | | |
|---|---|---|---|
| 3,992,520 | 11/1976 | Gwatkin | 424/172.1 |
| 4,299,916 | 11/1981 | Litman et al. | 435/6 |
| 4,978,611 | 12/1990 | Hosoda et al. | 435/7.92 |

FOREIGN PATENT DOCUMENTS

| | | |
|---|---|---|
| 0351045 | 1/1990 | European Pat. Off. . |
| WO8902743 | 4/1989 | WIPO . |

OTHER PUBLICATIONS

Stern et al., *J. Immunol.* 137(5):1604–1609 (1986).
Faulk et al., *Immunol. Rev.* 75:139–175 (1983).
Holers et al., *Immunol. Today* 6(6):188–192 (1985).
Reid et al., *Immunol. Today* 7(7&8):230–234 (1986).
Lublin et al., *Ann. Rev. Immunol.*, 7:35–58 (1989).
Fearon et al., *J. Exp. Med.* 153:1615–1628 (1981).
Griffin, Jr. et al., *J. Exp. Med.* 154:291–305 (1981).
Wright et al., *J. Exp. Med.* 156:1149–1164 (1982).
Seya et al., *J. Exp. Med.* 163:837–855 (1986).
Lublin et al., *J. Exp. Med.* 168:181–194 (1988).
Post et al., *FASEB J.* 3:A368 No. 828 (1989).
Demir, *The Mount Sinai J. of Med.* 56(2):141–146 (1989).
Cabot et al., *Biol. Reprod.* 19:666–672 (1978).
Suarez et al., *Biol. Reprod.* 27:473–483 (1982).
Eng et al., *Biol. Reprod.* 19:1083–1094 (1978).
Bedford et al., *J. Reprod. Fert.* 69:523;14 528 (1983).
Fahmi et al., *J. Dairy Sci.* 68:3318–3322 (1985).
Tauber et al., *Am. J. Obstet. Gynecol.* 151(8):1115–1125 (1985).
Isaacson et al., *J. Clin. Endocrinol. Metab.* 69(5):1003–1009 (1989).
Johnson et al., *Repro. Immunol.* 1989 pp. 169–176 (1990).
Ogbimi et al., *J. Repro. Immunol.*, 1;127–140 (1979).
Weir et al., *Handbook of Experimental Immunology*, (4th Ed.), Blackwell Scientific Publications, vol. 2: Cellular Immunology, pp. 55.12–55.18 (1986).
Yanagimachi et al., *Biol. Reprod.* 15:471–476 (1976).
Mao et al., *Am. J. Obstet. Gynecol.* 159:279–286 (1988).
Anderson et al., *J. Immunol.* 131(6):2908–2912 (1983).
Anderson et al., *Clin Exp. Immunol.* 43:99–108 (1981).
Wolf et al., *Biol. Reprod.* 32:1157–1162 (1985).
Yanagimachi, *Biol. Reprod.* 13:519–526 (1975).
Clark et al., *J. Immunol.* 117(4):1378–1386 (1976).
Yang et al., *Mol. Reprod. and Devel.* 27:118–129 (1990).
Downs et al., *Gamete Research* 15:115–122 (1986).
Nicolson et al., *J. Cell Biol.* 66:263–274 (1975).
D'Cruz et al., *J. Immunol.* 146(2):611–620 (1991).
Anderson et al., *J. Reprod. Immunol.* 10:231–257 (1987).
Anderson et al., *Biol. Reprod.* 41:285–293 (1989).
McLaughlin et al., *Int. J. Cancer* 30:21–26 (1982).
Purcell et al. Complement Inflammation, 6, #5, p. 390, Abstract 216 (1989) "The CD46 (July–m5) Antigen of Humans Incorporates Membrane Cofactor Protein (MCP) of Complement and Trophoblast–Leukocyte Antigen (TLX)".
O'Bryan et al "Human Seminal Clusterer" J. Clin Invest vol. 85 May 1990 pp. 1477–1486.
Clark et al "Generation of Neutrophil Chenotacfic Agent by Spermatozoa. . . " J. Immo. vol. 117 No. 4 Oct. 1978 pp. 1378–1388.
D'Cruz et al. "Eval. of Antisperm Complement Dep. Immune Mediators in Human Ovarian Fallecula Fluid" J. of Immuno. vol. 144 No. 10 May 1990 pp. 3841–3848.
Yanagimachi et al "Accel. of Acrosome Reaction and Activation of Guniea Pig Spermatozoa by Deagents and Other Reagents" Biology of Reprod. 13, 519–526 1975.
Husted. ACTA path. microbiol. scand. Sec. C. 83:338–346, 1975.

*Primary Examiner*—Toni R. Scheiner
*Assistant Examiner*—Lora M. Green
*Attorney, Agent, or Firm*—Sterne, Kessler, Goldstein & Fox

[57] ABSTRACT

Methods for detecting and isolating acrosome-reacted sperm and complement receptor-bearing oocytes using the complement component C3, fragments, or variants thereof, antibodies to a complement receptor, or antibodies to C3, are disclosed. These methods have application in the assessment of fertility, in the preparation of sperm or oocytes for in vitro fertilization or for gamete intrafallopian tube transfer, in promoting or inhibiting fertilization in vitro and in vivo, and in diagnosing and treating infertility.

5 Claims, 4 Drawing Sheets

COMPLEMENT COMPONENTS AND BINDING LIGANDS IN FERTILITY

STATEMENT OF GOVERNMENT RIGHTS IN THE INVENTION

The work performed during the development of this invention utilized funds provided by National Institutes of Health Grant No. CA-42738. The U.S. government has certain rights in the invention. This application is a continuation of application Ser. No. 07/487,039, filed Mar. 2, 1990, abandoned.

BACKGROUND OF THE INVENTION

1. Field of the Invention

The invention is in the field of mammalian reproduction and reproductive immunology and is directed to methods for detecting or isolating acrosome-reacted sperm and mature oocytes which are useful in diagnosis of infertility, for enhancement of in vitro fertilization, and for fertilization inhibition in vivo.

2. Description of the Background Art

Mammalian reproduction is a highly complex biological process which involves diverse specialized molecular systems. The importance of an immunological approach to reproduction stems from basic and clinical studies which demonstrated that reproductive cells and tissues express unique or shared molecules that can elicit immune responses, and that such immune responses can contribute to infertility.

Antibodies to Antigens of the Reproductive Tissues

One important approach to delineating the role of the immune system in reproduction has been the production and characterization of monoclonal antibodies (mAbs) for the identification, isolation, and characterization of mammalian, especially human, reproductive tissue antigens, and the use of such antibodies to block biological activities important in the reproductive process. (See, for example, Anderson, D. J. et al., *J. Reprod. Immunol.* 10:231–257 (1987)).

A number of mouse mAbs, such as, for example, H316, raised against syncytiotrophoblast plasma membranes from term human placentae, recognize the conserved region of a polymorphic cell surface molecule expressed by all human trophoblast populations, as well as peripheral blood leukocytes, certain specialized epithelia-including endometrial glands, and a number of malignant cell types (Johnson, P. M. et al., *Amer. J. Reprod. Immunol.* 1:246–254 (1981); McLaughlin et al., *Int. J. Cancer* 30:21 (1982); Bulmer et al., *Placenta* 6:127–40 (1985); Stern et al., *J. Immunol.* 137:1604 (1986)). The tissue distribution and biochemical characteristics of the H316-reactive antigen suggested a close relationship to the "TLX" (trophoblast/leukocyte-common or cross-reactive) antigen family, which had been speculated to induce blocking factors and recruit suppressor cells to the fetal-maternal interface during normal pregnancy. Polyclonal anti-TLX xenoantisera, which originally were used to characterize this antigen system, also react with human semen (Faulk et al., *Immunol. Rev.* 75:139 (1983); Bulmer et al., supra; Stern et al., supra)).

It has been speculated that the TLX antigen system, which may be recognized by the H316 antibody (Bulmer et al., supra; Stern et al., supra) plays a central role in the regulation of maternal-fetal immunological interactions (Faulk et al., supra). However, these regulatory mechanisms have not been clearly defined in pregnancy, nor have they been investigated in other cellular systems expressing these antigens.

The H316 mAb was included in a panel of anti-sperm monoclonal antibodies recently evaluated in a workshop sponsored by the World Healeth Organization (results reported in: Anderson et al. (1987), supra). This mAb (Workshop #S60) and another mAb included in a panel of anti-trophoblast mAbs, GB24 (Workshop #T22), from Dr. B. L. Hsi, Nice, France, appeared to react with the same antigen. H316 was found in this workshop to react with the acrosomal region of methanol-fixed epididymal and ejaculated sperm, as well as with sperm and germ cells in methanol-fixed frozen sections of adult and fetal human testis. The antibody did not react by radioimmunoassay (RIA) or immunofluorescence (IF) assays with surface antigens of unfixed, freshly ejaculated motile sperm. However, the antibody did react with acrosomal surface antigens on a majority of live motile sperm following either an 8 hour incubation with F-10 capacitation medium, or a 30 minutes incubation in medium containing the calcium ionophore, A23187, which also induces sperm acrosome reactions.

Complement Binding Proteins

A family of regulatory proteins that bind to and regulate various of the complement (C) proteins and peptides has been described (Holers, V. et al. *Immunol. Today* 6:188–192(1985); Reid, et al., *Immunol. Today* 7:230–223 (1986); Lublin, D. M. & Atkinson, J. P., *Ann. Rev. Immunol.* 7:35–58 (1989)). Among the C regulatory proteins are the receptor for C3b known as CR1, factor H of the alternate pathway, the C3b inactivator (I), decay accelerating factor (DAF), and gp45-70. The abbreviation CR will be used herein to signify C receptors and C regulatory proteins.

CR1 is an ~200 kD intrinsic membrane glycoprotein found on human erythrocytes, granulocytes, B lymphocytes, some T lymphocytes, monocytes, macrophages and glomerular podocytes. The role of CR1 in C-mediated endocytosis (Fearon, D. T. et al., *J. Exp. Med.* 153: 11615–1628 (1981)) and phagocytosis (Griffin, F. M. Jr. et al., *J. Exp. Med.* 154:291–305 (1981); Wright, S. D. et al., *J. Exp. Med.* 156:1149–1164 (1982)) is well known.

The local activation and deposition of C components is regulated in part by acceleration of the decay of the multicomponent complex known as C3 convertase, which is a necessary intermediary in C activation by the classical pathway and the alternate pathway. DAF, recognized for its role in accelerating decay of C3 convertase, is a 70 kD single chain intrinsic membrane glycoprotein present on erythrocytes, platelets and leukocytes. DAF binds with high affinity to C3b/C4b molecules only when they are in the membrane of the same cell as DAF, and its primary role is thought to be the prevention of the assembly of the convertase complex, rather than the dissociation of already formed complexes (Medof, M. E. et al., *Complement* 1:168 (1984)). CR1 also shares this decay accelerating activity.

Gp45-70 is identical to the membrane cofactor protein (MCP), which was named for its action as a co-factor in the factor I-dependent cleavage of C3b (Seya, T. et al., *J. Exp. Med.* 163:837–855 (1986)). This glycoprotein normally has a characteristic doublet protein band upon polyacrylamide gel electrophoresis (PAGE), with mean molecular weights of 58 and 63 kD. MCP was characterized as a cell-associated protein on the human monocyte-like cell line, U937, has cofactor activity but is not a classical C3b receptor. Antisera to human CR1, DAF, H, and two other C receptors, CR2 and CR3, do not cross react with MCP. The expression of CR1 and MCP on the cell surface appears to be reciprocal. MCP has been detected on human T and B lymphocytes, monocytes, platelets, epithelial cells, fibroblasts, and mononuclear-derived cell lines. The activity profiles of MCP and DAF are largely non-overlapping and complementary, leading to the suggestion that they act synergistically to prevent C activation on autologous tissues (Seya et al., supra).

More recently, the cDNA for MCP has been found to encode a protein having 4 short concensus repeats of about 60 amino acids rich in cysteine, the pattern of which is found in all C regulatory proteins studied. THe gene for MCP has been mapped to human chromosome 1 (q32), within 150 kilobases of the 3' end of the CR1 gene. The MCP cDNA also encodes two serine/threonine-reich regions, known sites for O-glycosylation (Lublin, D. M. et al., *J. Exp. Med.* 168:181–194 (1988); Post, T. W. et al., *FASEB J.* 3:A368 (1989) (abstr. #828)).

The link between MCP and fertility is discussed below.

Infertility

A large number of cases of human infertility, especially in the male, are not currently amenable to accurate diagnosis and the responsible mechanisms remain undetected. Indeed there is no practical gold standard for diagnosing male infertility. Clearly, multiple alterations in sperm anatomy and physiology can produce infertility. An urgent need exists in the art for new tests for diagnosing male and female infertility of various unknown origin. The invention disclosed herein is directed to such a need.

In Vitro Fertilization and Gamete Intrafallopian Tube Transfer

In vitro fertilization (IVF) and embryo transfer (ET), and gamete intrafallopian tube transfer (GIFT) wherein actual fertilization occurs in vivo, are gaining popularity as therapies for human infertility. The success of these procedures relies on various factors, not the least of which is the ability of the in vitro conditions, including the constitution of the synthetic medium, to promote the fertilization process. The media employed in these procedures were borrowed from other fields of tissue culture. It is thought that as the synthetic media more closely mimic the natural environment, the efficacy of IVF increases (Quinn, P. J. et al., *Fertil. Steril.* 44:493 (1985); Quinn, P. J., International Patent Publication WO 86/07377 (1986); Demir, R. H., Mt. Sinai J. Med. 56:141–146 (1989)). Considering the complexity of ovarian follicular fluid, fallopian tubal fluid, uterine and cervical mucus, and seminal fluid, there is an urgent need in the art to understand the constituents of these fluids and their respective roles in fertilization.

Complement and Fertilization

Oliphant and his colleagues (see, for example, Cabot, C. L. & Oliphant, G., *Biol. Reprod.* 19:666–672 (1978) and Suarez, S. S. & Oliphant, G., *Biol. Reprod.* 27:473–483 (1982)) have disclosed the presence of C components in bovine follicular fluid and their potential role in the reproductive process. For example, Cabot et al. (supra) demonstrated that antibodies to bovine C3 inhibited the ability of follicular fluid to induce the acrosome reaction in sperm, and suggested that the alternate pathway of C activation was involved in sperm capacitation. Suarez et al. (supra) found that C1q binds to washed ejaculated rabbit sperm, indicating the presence of bound immunoglobulins (i.e. antibodies). In the presence of serum containing active C components, C1q binding led C activation and ultimate damage and acrosomal loss. This potentially destructive process was shown to be inhibited by factors present in seminal plasma (Eng, L. A. & Oliphant, G., *Biol. Reprod.* 19:1083–1094 (1978)). It was therefore proposed that seminal plasma factors protect sperm both in the male reproductive tract and in proximal parts of the female reproductive tract (Suarez et al., supra) from C-mediated damage.

Bedford and Witkin (*J. Reprod. Fert.* 69:523–528 (1983)) reported that depletion of C in female rabbits in vivo before mating by treatment with cobra venom factor did not compromise the occurrence of the acrosome reaction after mating. This observation argues that the acrosome-reaction does not depend on C. However, C depletion resulted in a higher proportion of eggs fertilized, implying that C-mediated events may normally exert an inhibitory effect on sperm in the female reproductive tract.

Fahmi, H. A. et al. (*J. Dairy Sci.* 683318–3322 (1985)) showed that C levels (measured as total hemolytic C) in bovine follicular fluid varied over a 2–5 fold range with the estrus cycle, being highest at estrus and metestrus. At its peak, follicular C levels exceeded serum C levels by 5–22 fold. C3 production by uterine epithelial cells also appears to be under hormonal regulation. C3 transcript and protein levels increased after estradiol treatment in uterine epithelial cells, and this effect was inhibited by progesterone (Lyttle, C. R. et al., Complement Workshop, 1989)).

Tauber, P. F. et al. (*Am J. Obstet. Gynecol.* 151:1115–1125 (1985)) examined secretory proteins of the cervical, uterine, and fallopian tube mucosa in humans, and disclosed that relatively low levels of diffusible total C activity, and of C3 proteins, were present in these fluids. The levels varied both within and between organs. No role for C in the reproductive process was postulated, and a potential role for C as an anti-bacterial defense in the female reproductive tract was even discounted.

C has been postulated to play a role in endometriosis, a condition associated with female reproductive failure. Isaacson, K. B. et al. (*J. Clin. Endocrinol. Metab.* 69:1003–1009 (1989)) found that glandular epithelium of endometriotic tissue synthesized and secreted C3, which could be responsible directly, via its fragments or via other C activation products, for many of the immunological and inflammatory phenomena well-known in endometriosis.

In summary, the function of C, its components, or any of its receptors, binding or regulatory proteins, in the facilitation or inhibition of fertilization remains unknown. An understanding of how, when, and where C or C components function in reproductive processes, and an application of this knowledge to regulation and facilitation of fertilization, is a fundamental problem in the art to which the present invention is addressed.

SUMMARY OF THE INVENTION

This invention is based on the discovery by the inventors that sperm which have undergone an acrosome reaction express on their surface CR's variously known as TLX, MCP, gp45-70, or CD46, and that mature oocytes also express CR's on their surface. The inventors conceived of a role for sperm and egg CR's in the process of sperm-egg interaction during the fertilization process. The invention is therefore directed to the exploitation of the presence of these CR's on gametes in the diagnosis and treatment of infertility, in the identification of acrosome-reacted sperm and mature oocytes, in the isolation of acrosome-reacted sperm, in the promotion or inhibition of fertilization in vitro or in vivo.

More particularly, this invention is directed to a method for identifying an acrosome-reacted sperm comprising detecting the presence of a complement receptor on the sperm. In one embodiment, this method comprises the steps of: (a) contacting a sample with a binding partner for a complement receptor or for the complement component, C3b and (b) detecting the presence of the sperm-bound binding partner, thereby identifying the acrosome-reacted sperm.

The binding partner for this method includes C3b, a fragment of C3b such as iC3b, a variant of C3b, such as C3b dimer, an antibody specific for C3b, and an antibody specific for a complement receptor expressed on the sperm.

The binding partner is detectably labeled by any of a number of known labels, including enzymes, radioisotopes, fluorescent compounds, and chemiluminescent and bioluminescent compounds.

The invention is also directed to a method for isolating an acrosome-reacted sperm in a sperm-containing sample comprising separating sperm expressing a complement receptor from sperm not expressing the receptor. In one embodiment, this method comprises the steps of: (a) contacting a sample with a binding partner for a complement receptor or for complement component C3b; and (b) isolating the sperm bound to the binding partner. In another embodiment, the method further comprises treating the sperm-containing sample with an agent capable of inducing an acrosomal reaction prior to contacting with a binding partner. The isolation is achieved by using appropriately labeled binding partners, such as, for example, with iron, allowing magnetic separation of the sperm to which the binding partner has bound.

The invention is also directed to a method for identifying a complement receptor-bearing oocyte in an oocyte-containing sample comprising: (a) contacting the sample with a binding partner for a complement receptor or for complement component, C3b; and (b) detecting the presence of said oocyte-bound binding partner, thereby identifying the oocyte. In one embodiment, the method further comprising treating the oocyte with an agent capable of removing the zona pellucida from the oocyte.

The binding partner for this method includes C3b, a fragment of C3b, a variant of C3b, an antibody specific for C3b, and an antibody specific for a complement receptor expressed on an oocyte.

The binding partner is detectably labeled by any of a number of known labels, including enzymes, radioisotopes, fluorescent compounds, and chemiluminescent and bioluminescent compounds.

The invention is also directed to methods for promoting or inhibiting fertilization of an egg by a sperm in vitro or in vivo comprising contacting a sperm, an egg, or both with an amount of the complement component C3, or fragment or variant thereof, effective to promote or inhibit fertilization. In one embodiment, a C3b dimer at relatively high concentrations is used to inhibit fertilization. In another embodiment, an antibody to the sperm CR or to the egg CR is used to inhibit fertilization. In yet another embodiment, a relatively low concentration of the C3b dimer is used to promote fertilization.

This invention is directed to a method for diagnosing infertility in a male subject comprising detecting the presence of acrosome-reacted sperm in a sample obtained from the subject using the method described earlier. In one embodiment, the method further comprises contacting the sperm-containing sample with an agent capable of inducing an acrosomal reaction.

The invention is also directed to a method for diagnosing infertility in a female subject comprising detecting the presence of an oocyte expressing a complement receptor using the method described earlier or by measuring C3 levels in the reproductive tract.

The invention is also directed to method for treating infertility substantially associated with C3b in a subject comprising reducing the concentration of C3b in the reproductive tract fluid to a level sufficiently low to eliminate the fertilization inhibitory activity of the C3b.

BRIEF DESCRIPTION OF THE DRAWINGS

FIG. 1A. Intense fluoresence on developing acrosomal cap in condensing spermatids;

FIG. 1B. Fluorescence localized in acrosomes of mature spermatozoa.

FIG. 2A: Washed A23187-treated sperm, phase contrast microscopy;

FIG. 2B: Same field showing H316 binding to most sperm.

FIG. 4A: Spermatozoa with intact acrosomes did not show any binding of the antibody;

FIG. 4B: Spermatozoa that had undergone the acrosome reaction demonstrated binding of antibody to acrosomal contents and possibly to the inner acrosomal membrane.

DESCRIPTION OF THE PREFERRED EMBODIMENTS

Figure 1A:
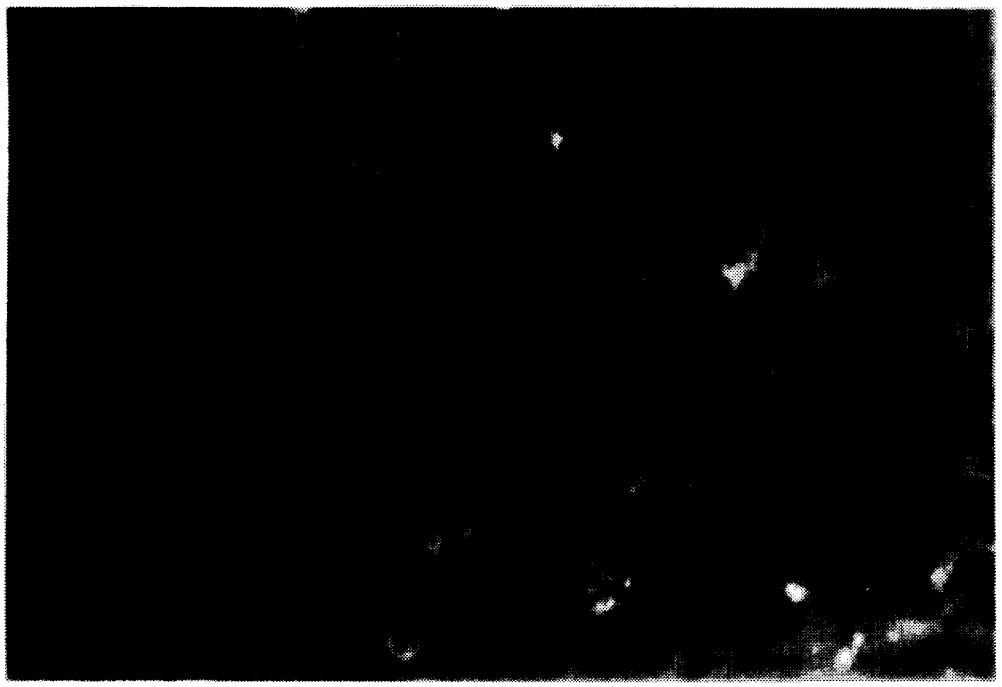
FIGS. 1A & 1B. Reactivity of H316 mAb on frozen sections of human adult testis as detected by indirect immunofluorescence (×600).

This invention is based on the recognition by the inventors that acrosome-reacted sperm bound to a mAb (H316) directed to a trophoblast cell surface antigen, and that the same antigen, present on leucocytes as well, was identical to a C binding protein, gp45-70, also known as the membrane cofactor protein (MCP). The antigen identified by the H316 mAb which is identical to MCP is also the same as the HuLy-m5 antigen (Johnson, P. M. et al., in: *Reproductive Immunology* 1989, Mettler & Billington (eds.), Elsevier, Amsterdam (in press). Under the current system of nomenclature, this antigen has been designated CD46. As a result of this discovery, the inventors conceived of a role for MCP, as a C binding protein or a C receptor (CR) on the surface of gametes, in the process of sperm-egg interaction during the fertilization process. The invention is therefore directed to the exploitation of the presence of this CR on gametes in the diagnosis of infertility, in the identification and isolation of acrosome-reacted sperm, in the promotion or inhibition of fertilization in vitro or in vivo, and in the treatment of infertility.

The term "complement" (C) refers to a group of proteins and glycoproteins normally found in the plasma and other body fluids of a mammalian organism (see, for example, Klein, J., *Immunology: The Science of Self-Nonself Discrimination*, John Wiley & Sons, New York, N.Y. (1982), pp. 310–346). These proteins undergo a cascade of reactions and interactions via two well-known pathways, the classical pathway and the alternate pathway, resulting in the generation of a variety of biologically active C components. One component, C3, is a 195 kD protein, which comprises two disulfide bridged chains of 105 and 75 kD. The enzymatically active C4-C2 complex, activated in the classical pathway by the binding of C1q to an antigen-antibody complex, cleaves C3 into two fragments, C3a and C3b. C3b, especially in the form of a complex with other C components, or chemically modified, such as in a dimer form, is capable of binding to CR's, such as the classically described CR1, CR2, and CR3, as well as to other more recently recognized C-binding and C-regulatory proteins, including DAF and MCP (Holers et al., supra, Seya et al., supra, Reid et al., supra, and Lublin & Atkinson, supra, which references are hereby incorporated by reference).

Therefore, as used herein, the term "complement receptor" refers to any molecule substantially associated with the surface of a cell which binds a natural C component, or binds a fragment, variant, or analogue of a natural C component. Intended to be included in the term "complement receptor" are the various C regulatory proteins. In particular, the CR associated with sperm is the MCP molecule, and is capable of binding C3b, preferably in the form of a C3b dimer. A CR is also capable of binding an antibody which is specific for the particular type of CR. Thus, for example, a spermatozoan binds to the H316 or GB24 mAb which are specific for the MCP-type of CR. Also intended within the scope of this invention are the CR's designated CR1, CR2, CR3 and CR4.

As used herein the term "C3" refers to the intact C3 molecule, whereas C3a and C3b are two fragments produced during C activation.

A "fragment" of C3 or C3b refers to any subset of the molecule, that is, a shorter peptide. Thus, C3b is a fragment of C3. Other fragments intended within the scope of this invention include iC3b, C3a, C3c, C3dg and C3d.

A "variant" of C3 or C3b refers to a molecule substantially similar to either the entire protein or a fragment thereof, which possesses biological activity that is substantially similar to a biological activity of C3 or C3b. Such biological activity includes the binding to a CR. A molecule is said to be "substantially similar" to another molecule if both molecules have substantially similar structures or if both molecules possess a similar biological activity.

Variants of C3b, for example, include C3b dimers, and higher oligomers. When C activation occurs at the cell-surface, multiple cycles of enzyme reactions result in the deposition on the surface of C3b in multimeric form. C3b dimers or higher oligomers indeed have higher affinity for CR's than do C3b monomers.

Variants of C3 or C3b are produced by chemical or recombinant means well-known in the art.

Such variants include, for example, deletions from, or insertions or substitutions of, amino acid residues within the amino acid sequence. Another group of variants are those in which at least one amino acid residue, and preferably, only one, has been removed and a different residue inserted in its place. Such substitutions preferably are made in accordance with the following list when it is desired to modulate finely the characteristics of a peptide molecule.

| Original Residue | Exemplary Substitutions | Original Residue | Exemplary Substitutions |
| --- | --- | --- | --- |
| Ala | gly; ser | Leu | ile; val |
| Arg | lys | Lys | arg; gln; glu |

-continued

| Original Residue | Exemplary Substitutions | Original Residue | Exemplary Substitutions |
| --- | --- | --- | --- |
| Asn | gln; his | Met | leu; tyr; ile |
| Asp | glu | Phe | met; leu; tyr |
| Cys | ser | Ser | thr |
| Gln | asn | Thr | ser |
| Glu | asp | Trp | tyr |
| Gly | ala; pro | Tyr | trp; phe |
| His | asn; gln | Val | ile; leu |
| Ile | leu; val | | |

Substantial changes in functional or immunological properties are made by selecting substitutions that are less conservative than those in the above list, that is, by selecting residues that differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. The substitutions that in general are expected to induce greater changes are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the protein molecule. However, when it is difficult to predict the exact effect of the substitution, deletion, or insertion in advance of doing so, one skilled in the art will appreciate that the effect will be evaluated by routine screening assays. For example, a change in the immunological character of the protein molecule, such as binding to a given antibody, is measured by an immunoassay such as a competitive type immunoassay.

An "analog" of C3 or C3b refers to a non-natural molecule substantially similar to either the entire molecule or a fragment thereof.

A "chemical derivative" of C3 or C3b contains additional chemical moieties not normally a part of the protein or fragment. Covalent modifications of the peptides are included within the scope of this invention. Such modifications may be introduced into the molecule by reacting targeted amino acid residues of the peptide with an organic derivatizing agent that is capable of reacting with selected side chains or terminal residues, as is well-known in the art (T. E. Creighton, *Proteins: Structure and Molecule Properties*, W. H. Freeman & Co., San Francisco, pp. 79–86 (1983)).

Derivatization with bifunctional agents is useful for cross-linking the proteins or fragments, to each other or to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl- 3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

The term "antibody" refers both to monoclonal antibodies (mAbs) which are a substantially homogeneous population and to polyclonal antibodies which are heterogeneous populations. Polyclonal antibodies are derived from the sera of animals immunized with an antigen. MAbs to specific antigens may be obtained by methods known to those skilled in the art. (See, for example Kohler and Milstein, *Nature* 256:495–497 (1975) and U.S. Pat. No. 4,376,110.) Such antibodies may be of any immunoglobulin class including IgG, IgM, IgE, IgA, IgD and any subclass thereof.

A mAb to the MCP protein, such as that recognized by mAb H316 is prepared in any of a number of ways according to methods known in the art. In one embodiment, mice serving as donors of spleen cells for hybridoma production are immunized with a membrane preparation of syncytiotrophoblast derived from human term placenta (Smith, N. C. et al., *Nature* 252:302 (1974); Ogbimi, A. O. et al., *J. Reprod. Immunol.* 1:127 (1979)). MAb's are prepared using standard techniques (see above), and screened by immunohistologic reactions and ELISA assays against the trophoblast membrane preparations, as described in detail in Johnson, P. M. et al. (1981), supra, which is hereby incorporated by reference.

In another embodiment, cDNA encoding the MCP protein, described in Lublin, D. M. et al., *J. Exp. Med.* 168:181–194 (1988) and Post, T. W. et al., (1989), supra (which references are hereby incorporated by reference), is expressed in *E. coli* using standard techniques (See: Maniatis, T., et al., In: *Molecular Cloning: A Laboratory Manual*, Cold Spring Harbor Press, Cold Spring Harbor, N.Y. (1984)), such that 5–20% of the total bacterial protein recovered is MCP. The bacterial lysate is electrophoresed using PAGE, the appropriate band cut, the protein eluted and prepared for immunization. Mice are immunized twice intraperitoneally with 50 μg/mouse. Their sera is tested for antibody activity by immunohistology or immunocytology on trophoblasts or on any other MCP-expressing cell and by ELISA with the bacterially expressed MCP. For immunohistological analysis, a biotin-conjugated anti-mouse immunoglobulin is used, followed by avidin-peroxidase, and a chromogenic peroxidase substrate. Such preparations are commercially available, for example, from ZYMED Corp., San Francisco, Calif.). Animals with serum antibodies are sacrificed 3 days later and their spleens taken for fusion and hybridoma production, as above. Positive hybridoma supernatants are tested by immunohistology or immunocytology and ELISA, as above, and by Western blot analysis or radioimmunoprecipitation.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of CR's or C components according to the methods disclosed herein in order to detect the presence of C components or CR on sperm or egg cells in the same manner as an intact antibody. Such fragments are typically produced by proteolytic cleavage, using enzymes such as papain (to produce Fab fragments) or pepsin (to produce F(ab')$_2$ fragments), using methods well-known in the art.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopic determinants usually consist of chemically active surface groupings of molecules such as amino acids or sugar side chains and have specific three dimensional structural characteristics as well as specific charge characteristics.

An "antigen" is a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence on a sperm or an egg of a CR or a C component bound to the receptor. Thus, the antibodies (or fragments thereof) useful in the present invention may be employed histologically to detect or visualize the presence of a CR or a C component. Thus, the presence of identifiable CR molecules on a acrosome-reacted spermatozoan may be used as a diagnostic test for infertility based on the reduced ability of deficient sperm to undergo the acrosome reaction. Similarly, the presence of identifiable C receptor molecules on an oocyte may be used as a diagnostic test for infertility based on the reduced ability of an oocyte to mature and express a CR.

Such an assay for binding of an antibody to a C receptor, antibody to a C component already bound to a C receptor, and the binding of a C component, such as C3b or a C3b dimer, typically comprises incubating a biological sample containing an egg or sperm from a subject in the presence of a detectably labeled binding partner, such as an antibody or C3b, and detecting the binding molecule which is bound in a sample.

Antibodies or their fragments, as well as the various complement components, fragments, and variants of this invention can be detectably labeled by any of a number of means well known in the art. Non-limiting examples of markers which serve as detectable labels include a radioisotope, an enzyme, a fluorescent label, a paramagnetic label, or a free radical.

Radioactive isotapes can be detected by such means as the use of a gamma counter or a scintillation counter or by autoradiography. A good description of a radioimmunoassay (RIA) may be found in *Laboratory Techniques and Biochemistry in Molecular Biology*, by Work, T. S., et el., North Holland Publishing Company, N.Y. (1978), with particular reference to the chapter entitled "An Introduction to Radioimmune Assay and Related Techniques" by Chard, T., incorporated by reference herein.

Examples of enzymes useful as markers include, but are not limited to, maleate dehydrogenase, staphylococcal nuclease, delta-5-steroidisomerase, yeast alcohol dehydrogenase, alpha-glycerolphosphate dehydrogenase, triosephosphate isomerase, horseradish peroxidase, alkaline phosphatase, asparaginase, glucose oxidase, betagalactosidase, ribonuclease, urease, catalase, glucose-6-phosphate dehydrogenase, glucoamylase, and acetylcholinesterase.

Examples of fluorescent compounds useful as markers include, but are not limited to, fluorescein isothiocyanate, rhodamine, phycoerythrin, phycocyanin, allophycocyanin, o-phthaldehyde, and fluorescamine, fluorescence emitting metals such as those of the lanthanide series. These metals can be attached to an antibody or C component using such metal chelating groups as diethylenetriamine pentaacetic acid (DTPA) or ethylenediaminetetraacetic acid (EDTA).

Examples of chemiluminescent compounds useful as markers include, but are not limited to luminol, isoluminol, aromatic acridinium ester, imidazole, acridinium salt, and oxalic ester.

Examples of bioluminescent compounds useful as markers include, but are not limited to, luciferin and aequorin.

The binding partners of this invention, such as C3, C3b, antibodies to C3, and antibodies to CR's can be directly labeled by the various markers mentioned above. In an alternate embodiment, they can be detected by labeling second binding partners capable of binding to the binding partners of the invention, which include Staphylococcus protein A, Staphylococcus protein G, anti-IgM or anti-IgG antibodies.

Also included in the scope of this invention are ligands such as the avidin-biotin pair, either of which can be detectably labeled or conjugated to the binding partners of this invention or their ligands.

Methods of making and detecting the antibodies and other binding partners of this invention, such as detectably labeled antibodies or C3b dimers, are well known to those of ordinary skill in the art, and are described in standard reference works including: Weir, D. M. et al. (eds.), Handbook of Experimental Immunology (Fourth Edition), Blackwell Scientific Publications, Oxford, 1986; Klein, J. *(Immunology: The Science of Self-Nonself Discrimination*, John Wiley & Sons, New York (1982)); Kennett, R., et al. (*Monoclonal Antibodies and Hybridomas: A New Dimension in Biological Analyses*, Plenum Press, New York (1980)); Campbell, A. ("Monoclonal Antibody Technology," In: *Laboratory Techniques in Biochemistry and Molecular Biology*, Volume 13 (Burdon, R., et al., eds.), Elsevier, Amsterdam (1984)); and Eisen, H. N., (In: *Microbiology*, 3rd Ed. (Davis, B. D., et al., Harper & Row, Philadelphia (1980)).

Various histological staining methods, including immunohistochemical staining methods, may also be used effectively according to the teaching of the invention. Such immunostaining methods useful in the present invention will be obvious to the artisan, the determination of which would not involve undue experimentation.

Appropriately labeled binding partners, such as C3 or C3b, antibodies to C3, or antibodies to CR's can be conjugated in such as way to provide a convenient means for isolating cells, e.g. sperm, to which the binding partner is bound. Thus, for example, an antibody or C3b dimer labeled with iron can be treated with a magnet or magnetic field to separate those sperm to which the iron-containing ligand is bound, using methods known in the art (Weir, D. M. et al. (eds.), Handbook of Experimental Immunology (Fourth Edition), Blackwell Scientific Publications, Oxford, 1986, pp. 55.12–55.18, which reference is hereby incorporated by reference). In an alternate embodiment, the binding partner or a second binding partner as described above can be attached to a solid support, such as Sepharose, dextran, Sephadex, collagen, polymethyl methacrylate, polystyrene, and the like, which can be used to isolate the labeled cell or sperm. Such methods are described in Weir, D. M. et al., supra.

The term "acrosome reaction" or "acrosomal reaction" refers to a reaction which a sperm undergoes naturally during the process leading up to fertilization. The reaction, which requires the presence of calcium ions is a morphological event in which the plasma membrane and the outer acrosomal membrane of the spermatozoan undergo a multipoint fusion (Green, D. P. L., In: Johnson, M. H., ed., *Development in Mammals*, North Holland, Amsterdam, 1978, Vol. 3, pp. 65–81)). This fusion, which is considered similar to the fusion of lysosomal membranes with a cell's plasma membrane, similarly leads to the release of hydrolytic enzymes contained within the acrosome (Akruk, S. R. et al., *Gamete Res.* 2:1–3 (1979). Among the released enzymes is acrosin. It is thought that elevation of calcium ions in the cytoplasm between the plasma and outer acrosomal membranes is the key event preceding the acrosome reactions. In the natural process, sperm undergo this reaction upon contact, with the zona pellucida, which is an acellular glycoprotein layer surrounding the oocyte. The hydrolytic enzymes permit penetration of the sperm through the zona pellucida to reach the oocyte membrane, where fusion occurs. Therefore, a viable acrosome reaction is an essential prerequisite for fertilization.

A number of techniques are known in the art for inducing an acrosome reaction under in vitro conditions (see, for example, Tomkins, P. T., International Patent Publication WO 89/02743 (1989), which is hereby incorporated by reference). These sperm treatment methods include, but are not limited to: (1) preincubation in simple or complex culture media supplemented with albumin or serum (Miyamoto, H. et al., *J. Reprod. Fert.* 32:193–205 (1973)); (2) exposure to high ionic strength media (Brackett, B. G. et al., *Biol. Reprod.* 12:260–274 (1972); (3) treatment with a calcium ionophore, such as A23187 (Aitken, R. J. et al. *J. Androl.* 56:321–329 (1984)); (4) direct microinjection of sperm (Lassalle, B. et al., *Gamete Res.* 16:69–78 (1987)); (5) exposure to phosphatidyl choline liposomes (Graham, J. K. et al., Biol. Reprod. 35:413–424 (1986)); (6) preincubation in simple medium supplemented with defined synthetic polymers and high calcium (Tompkins, P. T. et al., *Hum. Reprod.* 3:367–376 (1988)); (7) preincubation in the presence of glycosaminoglycans (Lee, C. N. et al., *J. Anim. Sci.* 63:861–867 (1986)); (8) preincubation for 48 hours at 4° C. in TEST-yolk buffer (Bolanos, J. R., *Fertil. Steril.* 39:536–540 (1983)); (9) electropermeabilization or electroporation by application of an electric field sufficient to raise the spermatozoal plasma membrane potential from about −70 mV to +1 V to allow an influx of calcium ions (Tompkins, P. T., 1989, supra); (10) addition of follicular fluid (Suarez, S. S. et al., *Gamete Res.* 14:107–121 (1986) and/or zona pellucida extract to a sperm suspension.

Fertilization by sperm can be tested in a number of ways. A preferred method employs the sperm penetration assay, known also as the hamster egg penetration test, the zona-free hamster ova assay, the hamster test, and the heterologous ovum penetration test (see, for example, Yanagimachi et al. (*Biol. Reprod.* 15:471–76 (1976), which is hereby incorporated by reference). Ova and attached cumulus cells are recovered from superovulated golden hamsters and treated with hyaluronidase (460 units, 1 mg/ml) to disperse the cumulus cells, and with trypsin (0.1%, 300 units/ml) to remove the zona pellucida. The test involves incubation of zona-free hamster eggs with sperm of any of a variety of species, preferably human sperm. The sperm penetrates the egg, and the assay is quantitated as the number or percent of eggs penetrated (containing at least one sperm head), or as a penetration index (number of penetrated sperm per number of eggs). This test is widely used as a means of evaluating male infertility in humans. It has also been used as a screening test for in vitro fertilization in order to identify male candidates whose sperm will be unlikely to fertilize human ova in vitro. While a very useful technique for measuring sperm-egg interactions, especially in the human where obtaining sufficient numbers of mature oocytes poses practical and ethical problems, the validity of this test as a clinical tool has been questioned (Mao, C. et al., *Amer. J. Obstet. Gynecol.* 159:279–286 (1988)).

By the term "promoting" fertilization is intended any treatment which will increase the ability of a sperm, normal or abnormal, to fuse with and penetrate an egg. The term "promoting" is intended to include any effects exerted on the sperm, on the egg, or both. In order to promote the fertilization process in vitro using the method of the invention, a binding partner for the sperm or egg CR is provided to sperm, an egg, or a sperm-egg mixture in a concentration effective to promote fertilization. Effective concentrations of the C3b dimer are in the range of about 0.1 to 100 µg/ml, preferably about 1 to about 50 µg/ml.

By the term "inhibiting" fertilization is intended any treatment which will decrease the ability of a sperm, normal or abnormal, to fuse with and penetrate an egg. The term "inhibiting" is intended to include any effects exerted on the sperm, on the egg, or both.

To inhibit fertilization, the C3b dimer is provided to sperm, an egg, or a sperm-egg mixture, in vitro or in vivo, in a concentration range of about 0.1 to about 10 mg/ml, preferably about 0.4 to about 5 mg/ml. Alternatively, a mAb specific for the sperm or egg CR is provided in a concentration range of about 0.1 to about 25 mg/ml, preferably about 0.5 to about 10 mg/ml.

The term "male reproductive tract" refers to the testes, epididymis, vas deferens, and urethra, and the associated tissues. "Male reproductive tract fluid" refers to semen or seminal plasma.

The term "female reproductive tract" refers to the vagina, cervix, uterus, fallopian tubes, ovaries, peritoneal cavity, and additional tissues and organs associated with the above. "Female reproductive tract fluid" refers to fluid secretions of the tissues and organs listed above, such as ovarian follicular fluid, fallopian tube fluid, uterine and cervical mucus, and the like.

The treatment of infertility associated with C3b refers to a condition in which activation of complement in the male or female reproductive tract, more commonly in the female reproductive tract, results in the present of sufficiently high levels of C3b or other C component capable of binding to sperm or egg CR's leading to inhibition of sperm-egg interactions. By reducing the level of the C component to sub-inhibitory concentrations, such as in the range of between about 0.1 to about 100 µg/ml, the fertilization process is promoted. This reduction in C levels or in C activation can be accomplished by providing the reproductive tract with an antibody to a C component, such as anti-C3, other C-inhibiting factors, or by down-regulating C production such as by endocrine regulation.

In an alternate embodiment, where infertility is associated with an insufficiency of a C component or components, or lack of C activation, such as in the female reproductive tract, it is possible, using the methods of the invention, to treat this infertility by promoting the activation of C or by providing the lacking CR-binding ligands, such as a C3b dimer. Contacting the female reproductive tract with C3b dimers in the concentration range of about 0.1 to about 100 µg/ml is expected to promote the fertilization process.

The methods of this invention are applicable to human and veterinary uses.

Having now generally described the invention, the same will be more readily understood through reference to the following example which is provided by way of illustration, and is not intended to be limiting of the present invention, unless specified.

EXAMPLE I

TROPHOBLAST/LEUKOCYTE-COMMON ANTIGEN (TLX) IS EXPRESSED BY HUMAN TESTICULAR GERM CELLS AND APPEARS ON THE SURFACE OF ACROSOME-REACTED SPERM

The mAb H316 was tested for its reactivity with human testis, epididymis, seminal plasma, and sperm to determine its reactivity pattern as well as to localize these antigens within male reproductive tract tissues. Because the H316-reactive antigen shows molecular weight polymorphism when precipitated from trophoblast and teratocarcinoma cell extracts, the molecular weight and charge of this antigen as expressed on sperm was also examined.

A. MATERIALS AND METHODS

1. Antibody

The H316 mouse mAb (IgG$_1$ isotype) was used in supernatant form for these studies. Details of its production and characterization are reported elsewhere (Johnson, P. M. et al., 1981, supra; McLaughlin et al., supra; Bulmer et al, supra; Stern et al., supra). A control murine IgG$_1$ isotype mAb reactive with an antigen expressed on sheep red blood cells (rbc) was kindly provided in supernatant form by Dr. Nancy J. Alexander (Norfolk, Va.); in addition, H315, another hybridoma supernatant specific for an irrelevant antigen, placental alkaline phosphatase, from the laboratory that produced H316, was used in some experiments. Both of the control antibodies were characterized in a recent WHO workshop and were documented not to be reactive with human sperm (Anderson et al., *J. Reprod. Immunol.* 10:231–57 (1987)).

2. Sperm Capacitation

Human semen from normal fertile donors was liquified at 37° C. for 30 min and diluted 1:5 in Biggers, Whitten and Whittingham (BWW) medium (Biggers et al., in: *Methods in Mammalian Embryology*, San Francisco, Freeman Press, pp. 86–116 (1971)). Sperm were isolated by centrifugation at 400×g, and were washed 3 times in BWW medium. Sperm at this point of preparation were termed "uncapacitated." Sperm were induced to capacitate and undergo an acrosome reaction by two protocols: 1) incubation at 37° C. for 6 h in BWW medium containing 3% human serum albumin (HSA ; Fraction 5, lot #36F-9333; Sigma Chemical Co., St. Louis, Mo.) (Byrd et al., *Biol. Reprod.* 34:859–69 (1986)), and 2) incubation for 2 h at 37° C. in BWW medium containing 3% HSA, followed by a 60-min incubation at 37° C. in 0.3% HSA and the calcium ionophore A23187 (obtained from Sigma Chemical Co.) at 5 mM, as described by Aitken et al. (*J. Androl.* 5:321–29 (1984)). Motile fractions of uncapacitated or capacitated/acrosome-reacted specimens were harvested following sperm swim-up from loose pellets into BWW/0.3% HSA medium. When uncapacitated and capacitated/acrosome-reacted fractions were tested in parallel, the uncapacitated/acrosome-reacted fractions were tested in parallel, the uncapacitated fraction was stored at 4° C. in BWW until the other fraction was ready.

3. Tissue Preparation

Fresh adult human testes and epididymides from surgical cases were kindly provided by W. C. DeWolf, Beth Israel Hospital, Boston, Mass. Fresh, 24-wk fetal testis was obtained at autopsy (provided by R. Berkowitz, Brigham and Women's Hospital, Boston, Mass.).

4. Immunofluorescence

Immunofluorescence was performed on frozen tissue sections and sperm smears as described previously (Anderson et al., *Clin. Exp. Immunol.* 43:99 (198)). Briefly, slides were air-dried, fixed in acetone for 10 min at room temperature, air-dried again, and stored sealed at −70° C. until use. Slides were incubated in phosphate-buffered saline/1% bovine serum albumin (PBS/BSA) for 5 min, then incubated with H316 mAb (diluted 1:10 in PBS/BSA) or control antibody for 30 min at room temperature. Slides were washed in PBS/BSA and then incubated with fluorescein-conjugated (FITC) rabbit anti-mouse IgG (Fab fragment, H- and L-chain-specific (Cappel, West Chester, Pa.), and diluted 1:40 in PBS/BSA for 30 min at room temperature. After a final wash, slides were mounted with a glycerol-based medium containing phenylene diamine (Sigma) and read immediately on a Zeiss epifluorescence microscope.

Viable motile sperm, obtained by swim-up technique, were pelleted by centrifugation at 400 ×g and resuspended in BWW/HSA medium containing a 1:10 dilution of antibody. Sperm were incubated at 37° C. in a 5% $CO_2$ incubator for 30 min at room temperature; motile spermatozoa (those remaining in suspension) were washed twice in PBS, air-dried onto slides, and fixed in acetone for 10 min at room temperature. The FITC-anti-mouse IgG was then applied, and the final steps of the procedure were as described above.

5. Radiolabeling of Cells

Cell-surface proteins were labeled with $^{125}I$ by a lactoperoxidase-catalyzed reaction (Michaelson et al., *Transpl. Proc.* 15:2033–38 (1983)). A23187-treated sperm ($5 \times 10^7$) were labeled in 1 ml PBS to which 200 µl of lactoperoxidase (Sigma; 1 mg/ml in PBS) and 1 mCi $Na^{125}I$ (IMA-30; Amersham, Arlington Heights, Ill.) were added, followed by 25 µl $H_2O_2$ (0.03% in PBS) added twice, 5 min apart. Radiolabeled cells were washed twice by centrifugation, membrane proteins were solubilized by resuspending the cell pellet in 2 ml of 0.5% NP-40 detergent (in PBS), cellular debris was pelleted and discarded, and the lysate was dialyzed overnight against PBS to remove residual free $^{125}I$. Lysates were then centrifuged once more to remove debris. Precipitation with trichloroacetic acid (5%) was then carried out on a 20-µl portion of each lysate to determine the amount of radiolabeled protein.

6. Immunoprecipitation

The immunoprecipitation procedure has been described in detail (Michaelson et al., supra). Each lysate was "cleared" by adding 50 µl rabbit anti-mouse IgG serum, followed 15 min later by 1.0 ml of sheep anti-rabbit Ig serum. Precipitation was allowed to proceed for 1 h at room temperature, followed by 1 h at 4° C. The amount and type of these reagents was critical for reducing the "background" yielded in subsequent precipitation. The clearing precipitate was pelleted and discarded. The lysates were then divided, and precipitation with antiserum was carried out: 20 µl of H316 supernatant was added, followed 15 min later by 100 µl of goat anti-mouse Ig serum (Pocono Rabbit Farms, Canadensis, Pa.). Precipitation was allowed to proceed at room temperature for 1 h, then overnight at 4° C.

Thorough washing of the immunoprecipitates was critical for minimizing the background. Precipitates were pelleted and resuspended in PBS. The pellets were broken into a fine suspension by repeated pipetting. The centrifugation and resuspension steps were repeated three times in 4 ml PBS, then once in 2 ml PBS. The centrifuge tubes were changed, and the precipitates were pelleted again. Care was taken to remove all visible liquid, and the pellets were dissolved in a solution containing 2% sodium dodecyl sulfate (SDS), tris(hydroxymethyl)aminomethane (pH 8.8), 5% mercaptoethanol, and 10% glycerin for SDS-polyacrylamide gel electrophoresis (PAGE), or alternatively, in a solution containing 50.5% urea, 5% mercaptoethanol, 2.5% NP-40, and 5% ampholines (LKB Corp., Rockville, Md.) for isoelectric focusing (IEF) gels. Samples in IEF buffer were left at room temperature for 1 h and then were frozen. Samples dissolved in SDS-PAGE buffer were placed in a boiling water bath for 3 min.

7. SDS-PAGE

Protein were electrophoresed in 10% acrylamide using a modified Laemmli system (see: Anderson et al., *J. Immunol.* 131:2908–12 (1983)). Molecular mass markers were added to outer lanes (β-galactosidase=116 kD; BSA=67 kD; ovalbumin=43 kD; carbonic anhydrase=29 kD; cytochrome C=13 kD (Sigma)). Gels were stained with Coomassie Brilliant Blue, dried on filter paper, and autoradiographed at −70° C. on Kodak type R film with a DuPont Cronex intensifying screen.

8. IEF

Precipitates, solubilized as described above, were also electrophoresed vertically on slab acrylamide IEF gels, adapted from the method of O'Farrell (*J. Biol. Chem.* 250:4007–4021 (1975)). Ampholine ranges of 3–10 and 5–7 were used in this study.

9. Radioimmunoassay (RIA)

RIAs were performed as described in Anderson et al. (supra). Briefly, viable spermatozoa were prepared as described above and suspended in Dulbecco's PBS/1% BSA. Spermatozoa ($10^6$) were pipetted into 96-well microtiter plates. After a 30-min incubation at 4° C. in 40 µl of serially diluted mAb, the cells were washed thrice in PBS/ 1% BSA and then incubated for 1 h at 4° C. with 200,000 cpm of $^{125}I$-labeled rabbit anti-mouse IgG that had been radiolabeled by the chloramine-T technique. After a final series of five washes, the cells from individual wells were assessed for bound reactivity in a Gamma Scintillation Spectrometer (Packard Instruments, Downer's Grove, Ill.).

10. Hamster Egg Penetration Test

Assessment of potential inhibitory activity of the H316 mAb in the hamster egg penetration test was performed blind in 3 independent laboratories according to the protocol originally described by Yanagimachi et al. (*Biol. Reprod.* 15:471–76 (1976)). Ova and attached cumulus cells were recovered from superovulated golden hamsters and treated with hyaluronidase (460 units, 1 mg/ml) and trypsin (0.1%, 300 units/ml) in BWW to disperse the cumulus cells and remove the zona pellucida, respectively. Twenty to thirty zona-free eggs were transferred to 100-µl aliquots containing BWW/HSA-capacitated spermatozoa, some of which had been treated with mAb for 6 h prior to the test then washed 3 times in BWW. Following insemination, the eggs were washed in BWW, mounted under a cover glass, and examined at 400×magnification with a phase-contrast microscope. The presence of a decondensing sperm head with an attached or closely associated sperm tail in the cytoplasm was considered a positive assay for fertilization. At least 20 eggs were scored for each test, and the penetration rates were calculated (Table 2).

11. Immunogold Technique/Transmission Electron Microscopy

Fresh, twice-washed, noncapacitated human sperm and calcium ionophore-treated sperm (as described above) were incubated with H316 or a nonsperm reactive $IgG_1$ mAb (Leu 3a+b, Becton Dickinson) at 4° C. for 30 min. They were then washed twice in cold BWW and incubated in a 1:5 dilution of 15 μM colloidal gold particle-conjugated goat antimouse Ig (Auroprobe EM G15, Janssen Life Sciences Products, West Chester, Pa.). Sperm were then washed twice in cold BWW and fixed in 2.5% glutaraldehyde in 0.1M phosphate buffer for 60 min at 4° C., followed by post-fixation with 1% osmium tetroxide in 0.1M phosphate buffer for 60 min at 4° C. The samples were then dehydrated through a graded series of acetones (50%, 70%, 95%×10 min and 100%×two 10-min session), and infiltrated with a 50:50 mixture of 100% acetone and Epon 812 (minus catalyst) for 24 h. Finally, the samples were embedded in Epon 812 (complete mixture), and thin sections were cut with an LTB Mark 2 ultra microtome. Section contrast was enhanced by sequential staining with a saturated aqueous solution of uranyl acetate (15 min) and lead citrate (15 min). The sections were then examined in a Philip's 410 electron microscope.

B. RESULTS

Figure 1B:
Figure 2A:
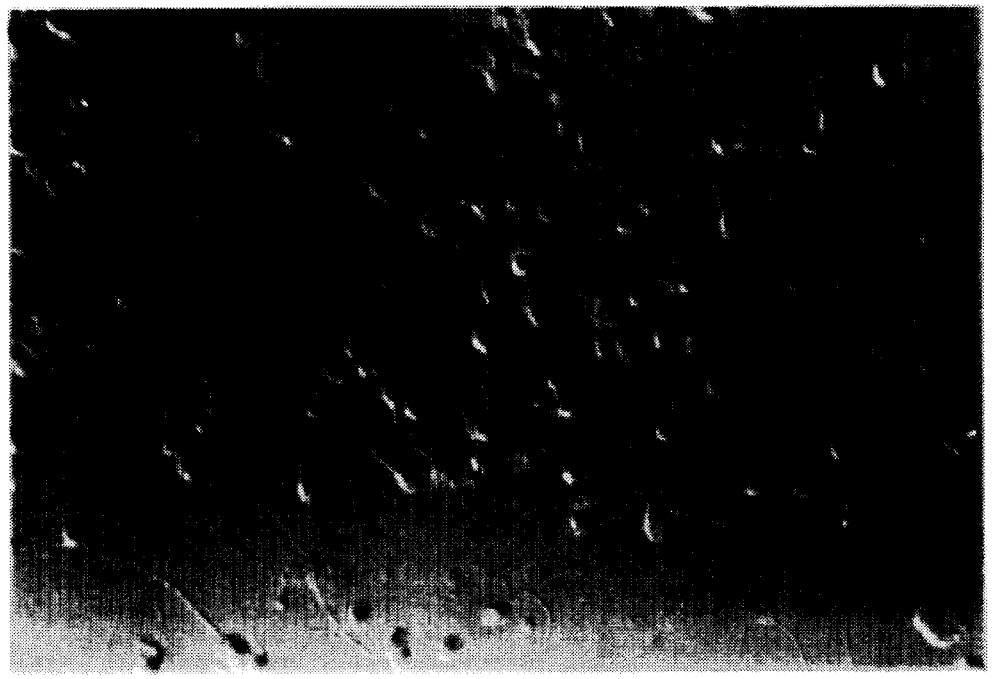
FIGS. 2A & 2B. Reactivity of H316 mAb to surface antigens on unfixed human ejaculate sperm detected by indirect immunofluorescence (×600).
Figure 2B:
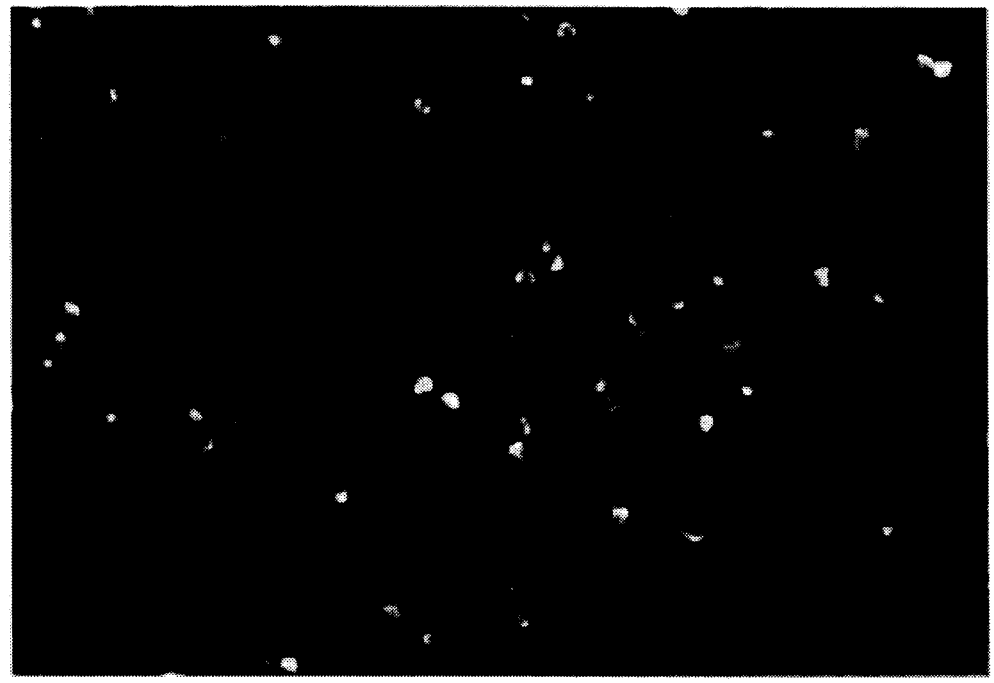

The H316 antibody reacted weakly with prespermatid immature germ cell forms in the human fetal and adult testis, and reacted intensely with the acrosomal region of condensing spermatids and mature spermatozoa in acetone-fixed testis and epididymal sections (FIG. 1). A majority of sperm in acetone-fixed, fresh washed human sperm smears were also positive for H316 in the acrosomal cap. Cell surface immunofluorescence performed on viable motile sperm revealed reactivity on sperm acrosomes for 18±8% of fresh uncapacitated sperm, 54±17% of incubation-capacitated sperm, and 62±18% of calcium-ionophore-capacitated sperm (FIGS. 2A & 2B). RIA performed on viable sperm also indicated an increased level of antibody binding associated with capacitation/acrosome reaction procedures (Table 1). Hamster egg penetration tests with H316 were performed in 3 independent laboratories (N. Alexander, Beaverton, Oreg., A. Hoffer, Boston, and N. Tanphaichitr, Boston, Mass.). Preincubation of sperm with H316 mAb at a dilution of 1:10 in BWW/HSA medium reduced sperm penetration in the hamster egg penetration test by a modest but significant amount; the mean inhibition was 38% (p<0.05). Ig subclass (anti-SRBC) and hybridoma media (H315) controls were not significantly inhibitory when tested at the same concentration in this assay (5% and 3% inhibition, respectively).

Figure 4A:
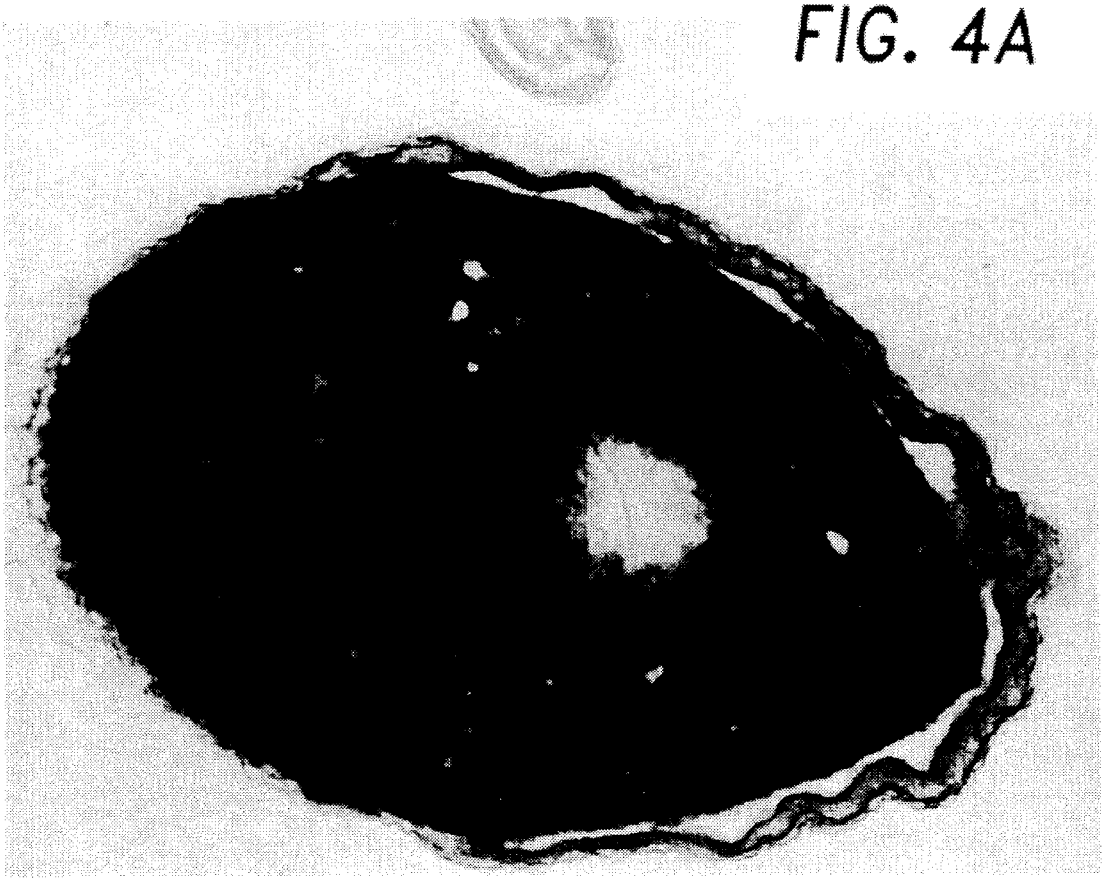
FIG. 4A & 4B. Immunogold detection of H316 binding to sperm using transmission electron microscopy (×48,000).
Figure 4B:
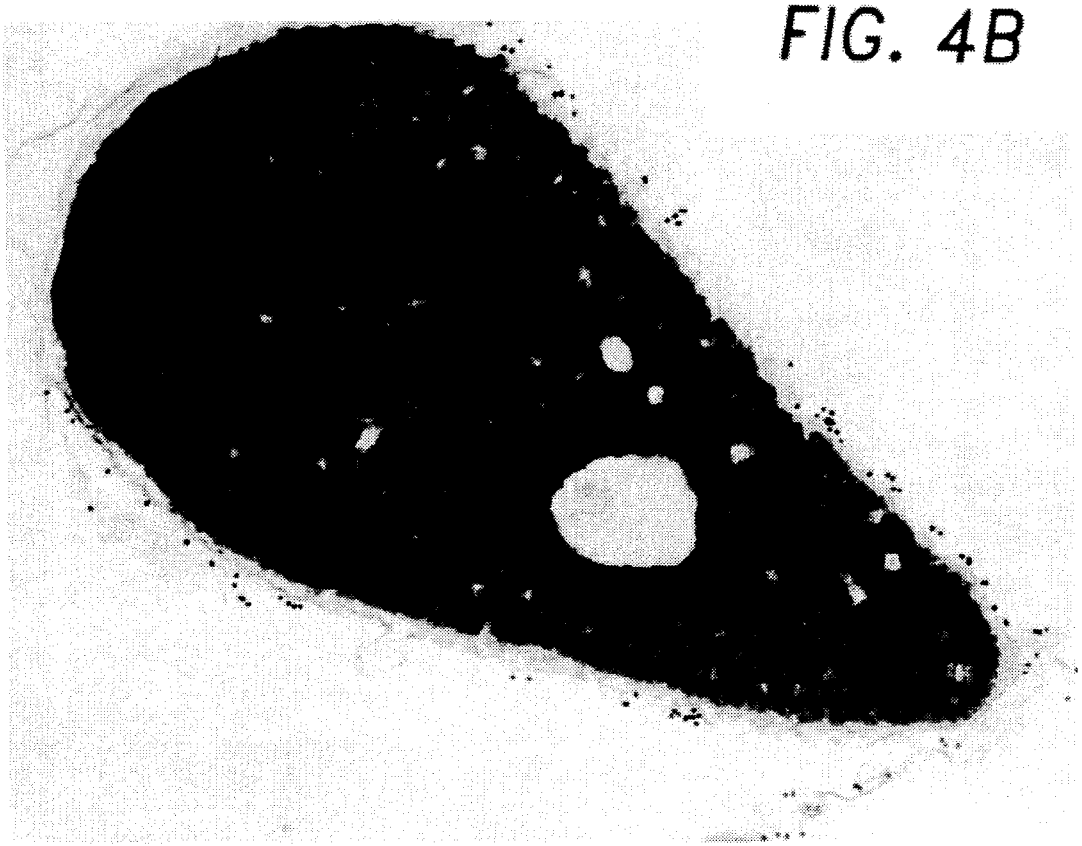

Immunogold antigen localization studies revealed no binding of H316 antibody to acrosome-intact sperm, and strong binding to acrosomal contents in ionophore-treated acrosome-reacted sperm (FIGS. 4A & 4B).

Figure 3:
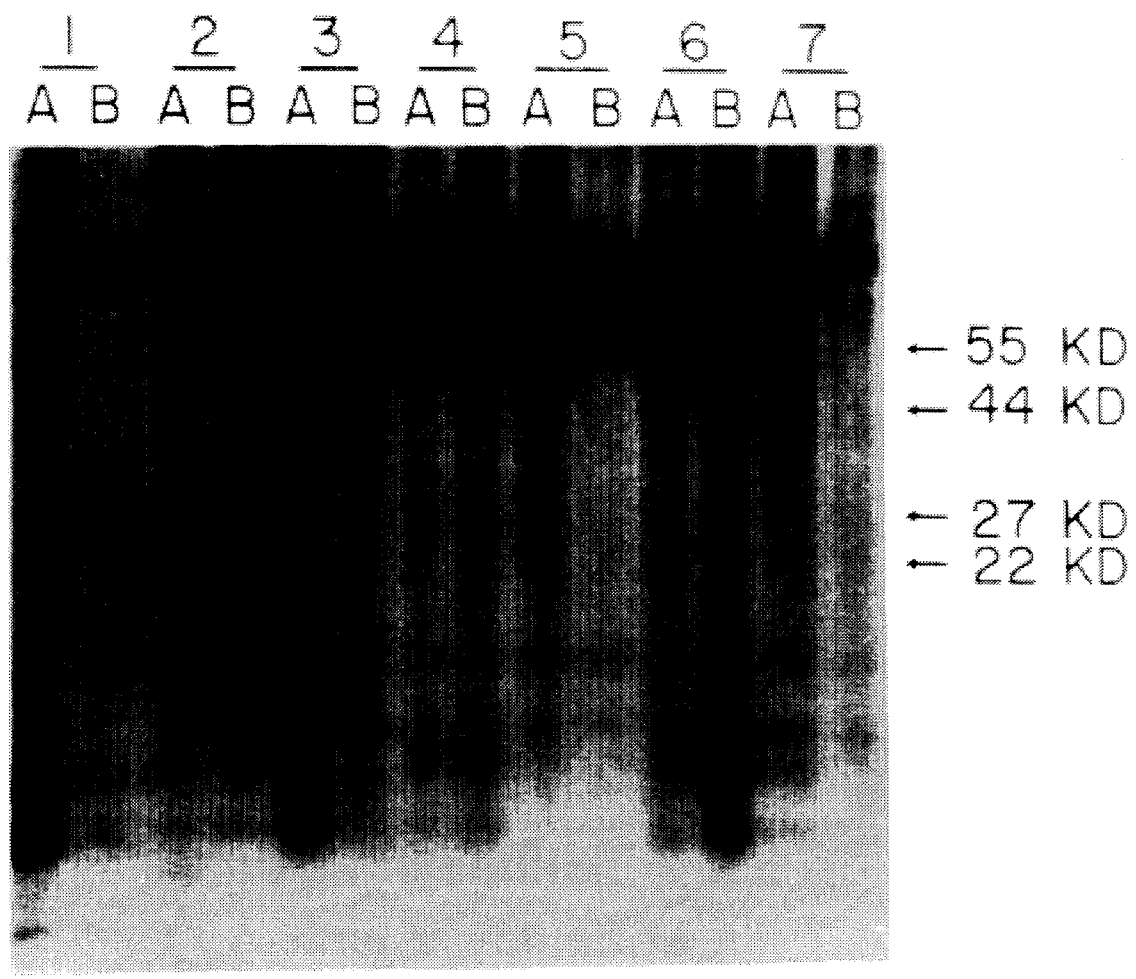
FIG. 3. H316 immunoprecipitates from $^{125}$I-surface-labeled A23187-treated human ejaculate sperm analyzed by SDS-PAGE under reducing conditions. Lane pairs 1–7 are from 7 different individuals. Lane A: specific H316 immunoprecipitate; Lane B: final pre-clear (background control).

A broad 50 kD band was immunoprecipitated by H316 in varying amount from $^{125}$I surface-labeled capacitated sperm from 10 individuals (data from 7 individuals shown in FIG. 3). IEF revealed several closely spaced bands in the 6–7 pI range, reminiscent of microheterogeneity due to post-translational modification (glycosylation, phosphorylation, etc.). Comparison of samples from 7 individuals did not reveal any variation in pI, although differences in quantity were noted (data not shown). Studies in other systems (see, for example, Michaelson et al., supra) have shown that this method is capable of resolving allelic forms of alloantigen molecules differing by a single charged amino acid interchange.

No immunogold labeling was observed in either sperm preparation when the Leu 3a+b mAb (IgG1 isotype negative control) was used in place of H316 as the primary antibody.

TABLE 1

REACTIVITY OF H316 WITH NON-CAPACITATED, HSA-CAPACITATED AND A23187 ACROSOME-REACTED HUMAN SPERM IN RIA

| | CPM bound[a] | |
|---|---|---|
| Sperm | H316 MAb | PBS/BSA control[b] |
| Noncapacitated sperm | 713 ± 71 | 104 ± 24 |
| BWW/HSA | 1984 ± 152* | 141 ± 35 |
| A23187 | 2207 ± 249* | 268 ± 41 |

[a]Mean ± SD of 3 separate experiments.
[b]PBS/BSA = phosphate-buffered saline/bovine serum albumin.
*Significantly different from noncapacitated sperm, p<0.01.

TABLE 2

EFFECT OF H316 ON HAMSTER EGG PENETRATION BY SPERM

| Treatment | % Eggs penetrated (% of control) | No. sperm/egg (% of control) |
|---|---|---|
| H316 mAb, 1:10 dilution | 62 ± 21* | 108 ± 0.2 |
| H316 mAb, 1:100 dilution | 92 ± 12 | 92 ± 1.8 |
| Anti-SRBC Mab, 1:10 dilution | 95 ± 9 | 95 ± 0.8 |
| Anti-SRBC Mab, 1:100 dilution | 104 ± 4 | 108 ± 0.2 |
| H315 mAb, 1:10 dilution | 97 | 89 |

Results are expressed as the mean ± SD of 5 separate experiments, except for the H315 mAb which was tested only once. The control values with no antibody present were 80 ± 6% eggs penetrated, 3.2 ± 1.4 sperm/egg.
*Significantly different from control (p<0.05).

C. DISCUSSION

The results of this study indicate that the antigen recognized by the H316 mAb is strongly expressed not only on human trophoblast, leukocytes, and certain neoplastic and epithelial cells, but also by human testicular germ cells and appears on the surface of acrosome-reacted sperm. Testicular germ cells do not undergo terminal differentiation until adulthood, and late-stage differentiation antigens expressed on post-meiotic testicular germ cells and spermatozoa are potential autoantigens. The antigen detected by H316 appeared to be weakly expressed by spermatogonia in the fetal testis, and therefore may not be a sperm autoantigen; however, the findings further indicate that H316 antigen expression is a common feature of cell types such as sperm and trophoblast, which are potential targets of immunological destruction due to expression of foreign differentiation or allotypic antigens.

The H316 antibody recognizes an antigen that appears to be size polymorphic between individual human trophoblast membrane preparations and neoplastic cell lines (Stern et al., supra). In contrast, the antigen expressed on human sperm consistently immunoprecipitated as a single broad protein band of approximately 50 kD. The broadness of this band could indicate glycosylation, which may mask molecular protein polymorphism of the sperm antigen; however, the molecular weight of the sperm antigen corresponds to a less glycosylated form of the H316 antigen than is precipitated from teratocarcinoma and choriocarcinoma cell lines (Stern et al., supra) and, hence, could indicate differential glycosylation of this molecule in human testicular germ cells, or a genetic alternative splicing mechanism operative in these cells, compared with other cell types.

The unexpected finding that binding of H316 to the human sperm surface occurs only after acrosomal changes induced by incubation in capacitation media or calcium ionophore treatment may provide a clue for understanding the functional significance of this antigen on sperm, and indicates that the antigen recognized by H316 may also be useful as a clinical marker for sperm capacitation or acrosome reaction. Another mAb described by Wolf et al., *Biol. Reprod.* 32:1157–62 (1985), recognizes a human acrosomal antigen that appears to be lost with capacitation/acrosome reaction (the reverse of that observed with H316). Expression of the H316 antigen on sperm from men with unexplained infertility, may serve as a diagnostic tool in understanding, as well as in diagnosing, male infertility. Furthermore, antibodies to she antigen recognized by H316 would be expected to inhibit sperm penetration of homologous eggs.

EXAMPLE II

A ROLE OF THE COMPLEMENT COMPONENT C3 AND ITS RECEPTOR, MCP, IN HUMAN SPERM-EGG INTERACTION

Based on the observation (Example I, above) that a 55 kD C3-binding protein, membrane cofactor protein (MCP) or CD46 is abundantly expressed on the surface of acrosome-reacted (AR) human sperm, and that mAb directed to this antigen inhibit the penetration of human sperm into hamster eggs, experiments were performed to test whether the MCP on human AR sperm is a functional receptor.

The binding of 125I-C3b dimers to AR sperm was analyzed. Table 3 shows the results of binding experiments indicating the specific binding of the labeled C3b dimers to AR sperm in comparisonvivo to acrosome-intact sperm and to polymorphonuclear (PMN) leucocytes. The affinity constant (Kd) of ligand binding to sperm or PMN's was calculated to be ~34 nm. Scatchard analysis revealed an approximately 8-fold increase in the number of C3b binding sites on AR sperm compared to acrosome-intact sperm (~280 binding sites/cell on AR sperm and ~36 sites/cell on acrosome-intact sperm). PMN had ~6788 sites per cell.

TABLE 3

SPECIFIC BINDING OF RADIOLABELED C3b DIMERS TO SPERM AND PMN's

| | $^{125}$I-[C3b]$_2$ added (µg/ml) | | | | |
|---|---|---|---|---|---|
| | 25 | 12.5 | 6.25 | 3.12 | 1.5 |
| Fresh Sperm | 0 | 0 | 306 | 82 | 355 |
| | | | (180) | (245) | (244) |
| AR Sperm | 2461 | 2378 | 615 | 159 | 0 |
| | | (837) | (335) | (352) | (121) |
| PMN's | 8184 | 6252 | 4211 | 4096 | ND |
| | (591) | (183) | (680) | (385) | |

Values shown are the means (±SEM) of specific binding in CPM. The specific binding was calculated by subtracting from the binding of labeled [C3b]$_2$ the binding in the presence of a 10-fold excess of unlabeled [C3b]$_2$. AR = acrosome-reacted; PMN = polymorphonuclear leukocytes; ND = not done Immunofluorescence (IF) staining of sperm were performed using murine mAbs against the 3 known types of C3 receptors, CR1, CR2, and CR3, along with fluoresceint-labeled second antibodies to detect the presence of known CRs. Indirect IF with C3b dimers and fluorescein-conjugated anti-C3 antibodies was used to assess C3b binding.

AR sperm did not express any of the more classic CR types, though they did stain with anti-MCP antibody (H316). Furthermore, binding of labeled C3b dimers to AR sperm was not inhibited by anti-C3 antibody, indicating that C3b bound to a C3b-binding moiety (Table 3).

Human and hamster eggs, prepared and freed of their zona pellucida (by low pH treatment and trypsin treatment, respectively) as described in Example I, above, were found to stain with anti-CR1 and anti-CR3 mAbs, and to bind C3b dimers as detected by staining with anti-C3 antibodies (Table 4). In contrast to AR sperm, eggs did not stain with anti-MCP (the H316 mAb). Therefore, human and hamster oocytes have C receptors on their surface different than the type associated with acrosome-reacted sperm.

IF assays further revealed the presence of C3-like molecules on the surface of hamster and human zona-free eggs which had been incubated in serum. Gametes were suspended in 100 µl of the appropriate buffers with predetermined saturating concentrations of mAb or C3b dimer. Cells were incubated at 20° C. for 60 min. and washed in buffer. Gametes were resuspended in 100 µl buffer with saturating concentrations of the second step reagent (FITC- or $^{125}$I-labeled goat anti-mouse IgG or rabbit anti-human C3) and incubated at 20° C. for 60 min. Gametes were washed an assessed for binding by IF microscopy or by counting bound $^{125}$I in a gamma counter. Non-specific binding was determined by primary incubation of replicate samples of gametes with equimolar concentrations of either subclass-matched IgG or nonspecific IgG.

Eggs showed abundant expression of C3 cross-reactive material on their surface.

TABLE 4

DETECTION OF C3 RECEPTORS ON SPERM AND EGGS BY IMMUNOFLUORESCENCE

| | Human Sperm | | Human | Hamster |
|---|---|---|---|---|
| | Fresh | AR* | Eggs | Eggs |
| anti-CR1 | − | − | ++ | ++ |
| anti-CR2 | − | − | ± | − |
| anti-CR3 | − | − | ++ | ++ |
| anti-MCP | − | ++ | − | − |
| anti-DAF | − | ± | − | − |
| C3b$_2$, anti-C3 | − | ++ | ++ | ++ |

*Acrosome-reacted sperm
Scoring: −: no detectable fluorescence; ±; intermediate staining; ++: strong staining These results indicate that both sperm and egg membranes have the capacity to bind C3b, suggesting that this component of activated complement, presumably in complex form, serves as a bridge between a sperm and an oocyte, via dissimilar receptors on the two gametes. Complement, specifically the C3 fragment, C3b, plays an important role in the fertilization process.

This is further supported by results of experiments which examined the effect on the hamster egg penetration test of C3b dimers, an antibody to the MCP-type CR (H316), and an anti-C3 antibody. Results with sperm from fertile donors (Table 5) indicate that low concentrations of the C3b dimer, at 4 and 40 µg/ml, significantly enhance fertilization, whereas a higher concentration of C3b dimer, 400 µg/ml, markedly inhibited fertilization. Antibody to C3 (at 10 mg/ml) also inhibited fertilization. Fertilization by sperm from subfertile donors was enhanced by 40 µg/ml of C3b dimer whereas both an antibody which binds to the CR on acrosome-reacted sperm (H316) and an anti-C3 antibody were highly inhibitory to the fertilization process (Table 6).

TABLE 5

EFFECT OF $C3b_2$ AND mAb H316 ON HAMSTER EGG PENETRATION: FERTILE DONOR SPERM

| Treatment | No. Eggs | Eggs Penetrated/ Total (%) | Penetration Index |
|---|---|---|---|
| Control (no treatment) | 23 | 19/23 (82.6%) | 1.91 |
| H316 (0.1 mg/ml) | 21 | 19/21 (90.5%) | 1.10 |
| C3b dimer (0.004 mg/ml) | 25 | 23/25 (92%) | 2.84* |
| C3b dimer (0.04 mg/ml) | 24 | 22/24 (91.7%) | 3.85* |
| C3b dimer (0.4 mg/ml) | 23 | 17/23 (73.9%) | 0.96* |
| anti-C3 (0.1 mg/ml) | 27 | 12/27 (44%) | 0.81* |

Penetration Index - # penetrated sperm/# eggs
*Significantly different from control.

TABLE 6

EFFECT OF $C3b_2$ AND mAb H316 ON HAMSTER EGG PENETRATION: SUBFERTILE DONOR SPERM

| Treatment | No. Eggs | Eggs Penetrated/ Total (%) | Penetration Index |
|---|---|---|---|
| Control (no treatment) | 21 | 7/21 (33%) | .43 |
| H316 (0.1 mg/ml) | 14 | 0/14 (0%) | 0* |
| C3b dimer (0.004 mg/ml) | 18 | 9/18 (50%) | .50 |
| C3b dimer (0.04 mg/ml) | 20 | 10/20 (50%) | .60* |
| C3b dimer (0.4 mg/ml) | 18 | 5/18 (28%) | .39 |
| anti-C3 (0.1 mg/ml) | 12 | 1/12 (8%) | .08* |

Penetration Index - # penetrated sperm/# eggs. Subfertile donor sperm consistently performed poorly (<50% penetration).
*Significantly different from control.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for detecting an oocyte bearing complement receptor 1, complement receptor 2, or complement receptor 3, in an oocyte-containing sample, said method comprising:

(a) contacting said sample with a specific binding partner for complement receptor 1, complement receptor 2, or complement receptor 3, or with a specific binding partner for complement component C3 or a fragment or variant of complement component C3; and (b) detecting the presence of said specific binding partner bound to said oocyte in said sample.

2. The method of claim 1, wherein said binding partner is selected from the group consisting of: an antibody specific for complement receptor 1, complement receptor 2, or complement receptor 3; C3b; a biologically active fragment or derivative of C3b; and C3b and an antibody specific for C3b.

3. A method for screening for infertility by detecting an oocyte bearing complement receptor 1, complement receptor 2, or complement receptor 3 in an oocyte-containing sample, said method comprising:

(a) contacting said sample with a specific binding partner for complement receptor 1, complement receptor 2, or complement receptor 3, or with a specific binding partner for complement component C3 or a fragment or variant of complement component C3; and (b) detecting the presence of said specific binding partner bound to said oocyte in said sample; and (c) quantitating the amount of bound specific binding partner detected in said sample (b) as an indication of infertility.

4. The method of claim 3, wherein said binding partner is selected from the group consisting of: an antibody specific for complement receptor 1, complement receptor 2, or complement receptor 3; C3b; a biologically active fragment or derivative of C3b; and C3b and an antibody specific for C3b.

5. The method of either of claims 1 or 3 further comprising before step (a) treating said oocyte with an agent capable of removing the zona pellucida from said analyte.

* * * * *